United States Patent
Barker et al.

(10) Patent No.: US 11,490,866 B2
(45) Date of Patent: Nov. 8, 2022

(54) METHODS AND SYSTEMS FOR COOLING OF AN IMAGING SYSTEM

(71) Applicant: GE Precision Healthcare LLC, Milwaukee, WI (US)

(72) Inventors: David Barker, Salt Lake City, UT (US); Nathan Pack, South Jordan, UT (US)

(73) Assignee: GE Precision Healthcare LLC, Milwaukee, WI (US)

( * ) Notice: Subject to any disclaimer, the term of this patent is extended or adjusted under 35 U.S.C. 154(b) by 226 days.

(21) Appl. No.: 16/690,107

(22) Filed: Nov. 20, 2019

(65) Prior Publication Data

US 2021/0145380 A1 May 20, 2021

(51) Int. Cl.
*H01J 35/10* (2006.01)
*A61B 6/00* (2006.01)

(52) U.S. Cl.
CPC .......... *A61B 6/4405* (2013.01); *A61B 6/4441* (2013.01); *A61B 6/4488* (2013.01)

(58) Field of Classification Search
CPC ....... A61B 6/032; A61B 6/037; A61B 6/4405; A61B 6/4441; A61B 6/447; A61B 6/4488; A61B 17/24; A61B 18/04; A61B 2017/00084; A61B 2017/00274; A61B 2017/00809; A61B 2017/00818; A61B 2017/4216; A61B 2018/00285; A61B 2018/00488; A61B 2018/00494; A61B 2018/00541; A61B 2018/00547; A61B 2018/00559; A61B 2018/00577; A61B 2018/00642; A61B 6/035; A61B 6/40; A61B 6/4423; A61B 6/56; A61B 6/107; A61B 6/4021; A61B 6/4028; A61B 6/4233; A61B 6/0487; A61B 6/06; A61B 6/4007; A61B 6/4035; A61B 6/405; A61B 6/4411; A61B 6/482; A61B 6/504; A61B 6/54; A61B 6/587; A61B 6/4452; A61B 6/4458; A61B 6/467; A61B 34/25; A61B 90/98; A61B 6/464; A61B 6/462; A61B 6/463; A61B 6/08; A61B 6/466; A61B 6/548; A61B 6/0492; A61B 6/589; A61B 6/465; A61B 6/4482; A61B 6/582; A61B 6/487; A61B 6/5205; A61B 6/44; A61B 6/5211; A61B 6/566; A61B 6/563; A61B 6/4447; A61B 6/508; A61B 6/5235; A61B 6/544; A61B 6/42; A61B 6/025; G01R 33/28;

(Continued)

(56) References Cited

U.S. PATENT DOCUMENTS 5,548,628 A 8/1996 Eggleston et al.
6,366,642 B1 4/2002 Andrews
(Continued)

FOREIGN PATENT DOCUMENTS

DE 102013218285 A1 * 3/2015 ............. H05G 1/025

Primary Examiner — Irakli Kiknadze (57) ABSTRACT

Various systems are provided for an X-ray system. In one example, a mobile X-ray system, comprises a moveable arm comprising an X-ray source arranged at a first end and an X-ray detector arranged at a second end. The mobile X-ray system further comprises an integrated, fluid-circulating cooling arrangement arranged within a housing shared with the X-ray source, wherein passages of the cooling arrangement do not extend outside the housing.

20 Claims, 5 Drawing Sheets

(58) Field of Classification Search
CPC ............. G01R 33/3804; G06N 3/0445; G06N 3/0454; G06N 3/0472; G06N 3/08; G16H 40/40; H01J 2235/1287; H01J 2235/1208; H01J 2235/1291; H01J 35/10; H01J 35/106; H01J 35/107; H01J 2235/1204; H01J 2235/1262; H01J 35/16; H01J 2235/1283; H01J 35/18; H01J 35/1017; H01J 35/1024; H01J 2235/1013; H01J 2235/1216; H01J 2235/122; H01J 2235/1275; H01J 2235/068; H01J 2235/081; H01J 35/13; H01J 7/26; H01J 19/36; H01J 19/54; H01J 19/74; H01J 2229/0061; H01J 2229/863; H01J 2229/8638; H01J 2235/12; H01J 35/065; H01J 35/24; H01J 5/02; H01J 1/025; H01J 35/025; H01J 2235/162; H01J 35/26; H01J 35/305; H01J 35/30; H01J 35/153; H01J 35/147; H01J 35/14; H01J 35/08; H01J 35/06; H01J 35/02; H05G 1/02; H05G 1/025; H05G 1/04; H05G 1/36; H05G 1/54; H05G 1/06; H05G 1/08; H05G 1/10; H05G 1/20; H05G 1/26; H05G 1/34; H05G 1/52; H05G 1/60; H05G 1/66; H05G 1/32; H05G 1/58; H05G 1/12; H05G 1/70; G01N 2223/076; G01N 2223/419; G01N 23/046; G01N 23/223; G01N 23/083; G01N 23/12; G01N 2223/3103; G01N 2223/643; G01N 2223/612; G01N 27/06; G01N 23/04; G21K 1/02; G21K 1/06; G21K 1/025; G21K 1/10; A61N 5/01; A61N 5/10; F04D 25/00; F04D 29/58; G06F 3/04812; G06F 3/0487; G06F 3/011; G06F 3/0484; G06F 3/04815; A61F 9/029; G06T 19/006; G01B 15/02; G01B 15/025
USPC .......................................... 378/130, 199, 200
See application file for complete search history.

(56) References Cited

U.S. PATENT DOCUMENTS

| | | | |
|---|---|---|---|
| 6,519,317 B2 | 2/2003 | Richardson et al. | |
| 6,608,429 B1 | 8/2003 | Snyder | |
| 7,174,001 B2* | 2/2007 | Andrews | H05G 1/025 378/141 |
| 10,820,871 B1* | 11/2020 | Martinez Ferreira | A61B 6/4441 |
| 2004/0196959 A1* | 10/2004 | Weston | H05G 1/02 378/141 |
| 2005/0117706 A1* | 6/2005 | Powell | A61B 6/037 378/141 |
| 2008/0304625 A1* | 12/2008 | Dehler | A61B 6/4488 378/197 |
| 2010/0111259 A1* | 5/2010 | Van Der Ende | H05G 1/025 378/142 |
| 2015/0319831 A1* | 11/2015 | Fehre | H05G 1/02 378/62 |
| 2019/0101332 A1* | 4/2019 | Schmidt | F27D 21/00 |

* cited by examiner

METHODS AND SYSTEMS FOR COOLING OF AN IMAGING SYSTEM

TECHNICAL FIELD

Embodiments of the subject matter disclosed herein relate to a fluid-circulating heat exchanger arranged adjacent to an X-ray source of a mobile X-ray system.

DISCUSSION OF ART

An X-ray imaging system comprises an X-ray source and an X-ray detector. X-rays emitted from the X-ray source can impinge on the X-ray detector and provide an X-ray image of an object or objects that are placed between the X-ray source and the detector. An imaging assembly may comprise a moveable support for adjusting an imaging angle and/or position. Additionally or alternatively, the X-ray source and the X-ray detector may be arranged on a main body of the X-ray imaging system, wherein the main body may be moveable relative to the moveable support.

During a scanning event, the X-ray source may demand cooling due to heat build up caused by high amounts of current flowing therethrough. A fluid-circulating cooling device, such as a heat exchanger, may be configured to flow coolant to the X-ray source.

BRIEF DESCRIPTION

In one embodiment, a mobile X-ray system, comprises a moveable arm comprising an X-ray source arranged at a first end and an X-ray detector arranged at a second end, and a cooling arrangement arranged within a housing shared with the X-ray source, wherein passages of the cooling arrangement do not extend outside the housing.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

The following description relates to embodiments of a mobile X-ray system comprising a cooling arrangement. In one example, the cooling arrangement is arranged only in a moveable, imaging portion of the X-ray system. More specifically, the cooling arrangement is arranged directly adjacent to an X-ray source at a first end of an arm of the X-ray system. The cooling arrangement and the X-ray source may share a common housing (e.g., a casing). In one embodiment of the present disclosure, the common housing may partially seal the cooling arrangement and the X-ray source from atmosphere. In one example, the housing may seal only the X-ray source from atmosphere, while a portion of the housing containing the entirety of the cooling arrangement may comprise a vent or other opening. As such, outside of an opening to direct radiation to an X-ray detector of the X-ray system, the common housing and portion of the arm in which the X-ray source is arranged may be completely sealed.

Unlike stationary X-ray imaging systems with very large integrated cooling systems, mobile X-ray imaging systems demand smaller cooling devices due to limited packaging space and to decrease weight for transport when the mobile X-ray imaging system is moved. The mobile X-ray imaging system may comprise a first moveable portion configured as an arm with an X-ray source and X-ray detector. The mobile X-ray imaging system may further comprise a second moveable portion, such as a wheeled structure, allowing an entirety of the mobile X-ray imaging system to move. In one example, the mobile X-ray imaging system may be moved (e.g., rolled) within different portion of a single room or to separate rooms of a plurality of rooms of a building.

As used herein, mobile radiographic imaging systems will be understood to include imaging systems wherein the imaging components of the imaging system are moveable and/or imaging systems wherein the imaging system itself may be moved from location to location via a mobile support system (e.g., a plurality of wheels, rails, etc.). Although the cooling arrangement is described herein as configured to decrease temperatures of a C-arm imaging system, it will be appreciated that in some examples, the cooling arrangement may be employed with a different radiographic imaging system, such as an industrial imaging system (non-medical), an immobile imaging system wherein one or more components of the imaging system is repositionable, or an imaging system of a different imaging modality (e.g., visual, positron emission tomography, magnetic resonance imaging, computed tomography, etc.).

A demand for the cooling arrangement on mobile X-ray imaging systems may arise from continued developments in X-ray technology leading to increased current demands and smaller packaging sizes. Such developments may lead to increased cooling demands to accommodate increases in temperature while blocking thermal transfer from the X-ray source to neighboring components.

Previous examples of cooling arrangements included arranging a radiator of the cooling arrangement on a support of the arm, and routing cooling passages from the support through a support structure and into the portion of the arm where the X-ray source is located. However, such examples are inefficient, expensive to maintain and manufacture, and reduce the mobility of the X-ray system. Further examples include arranging the cooling arrangement in the arm, with cooling passages extending through an entire body of the arm. For example, this may include routing cooling passages from a first end of a C-arm to a second end, opposite the first end, of the C-arm. While mobility may be maintained in such examples, the cost of manufacture is still relatively high. Furthermore, a short-coming present in both previously described examples includes where the cooling arrangements are not configured to sufficiently cool the X-ray source independently. As such, a housing for the X-ray source in the previous examples comprises one or more openings for allowing the X-ray source to be at least partially cooled by atmospheric air. One issue with this approach is an increased packaging size as the X-ray source is arranged completely outside the main body of the arm to allow sufficient air flow to the X-ray source to achieve a desired cooling. Furthermore, cooling via ambient air may still be insufficient, increasing a likelihood of degradation. By doing this, the X-ray source is closer to the detector and a patient to be scanned, which may increase an X-ray dose received by the patient.

Figure 1:
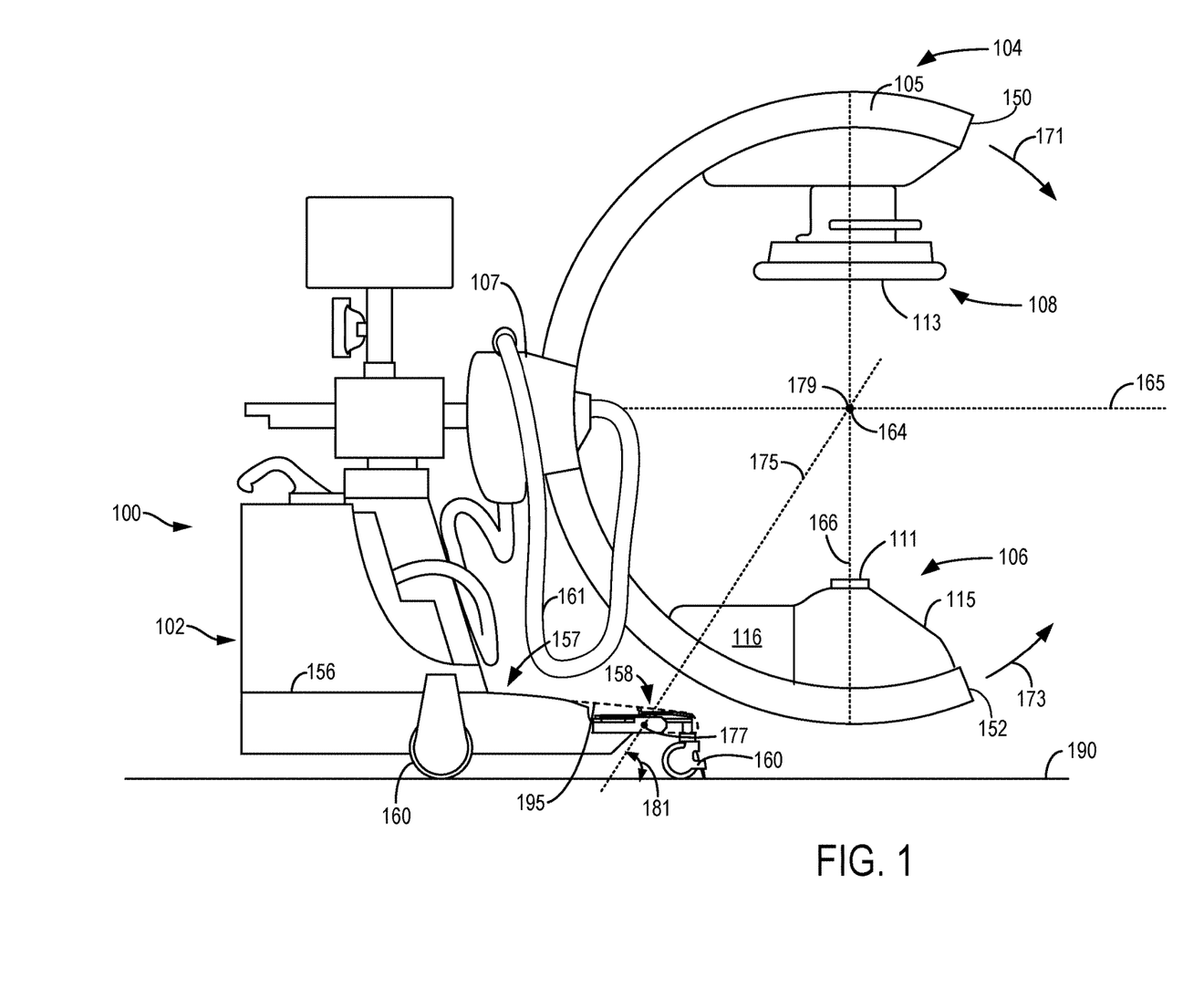
FIG. 1 is a side view of a medical imaging system including a C-arm, according to an embodiment.
Figure 2:
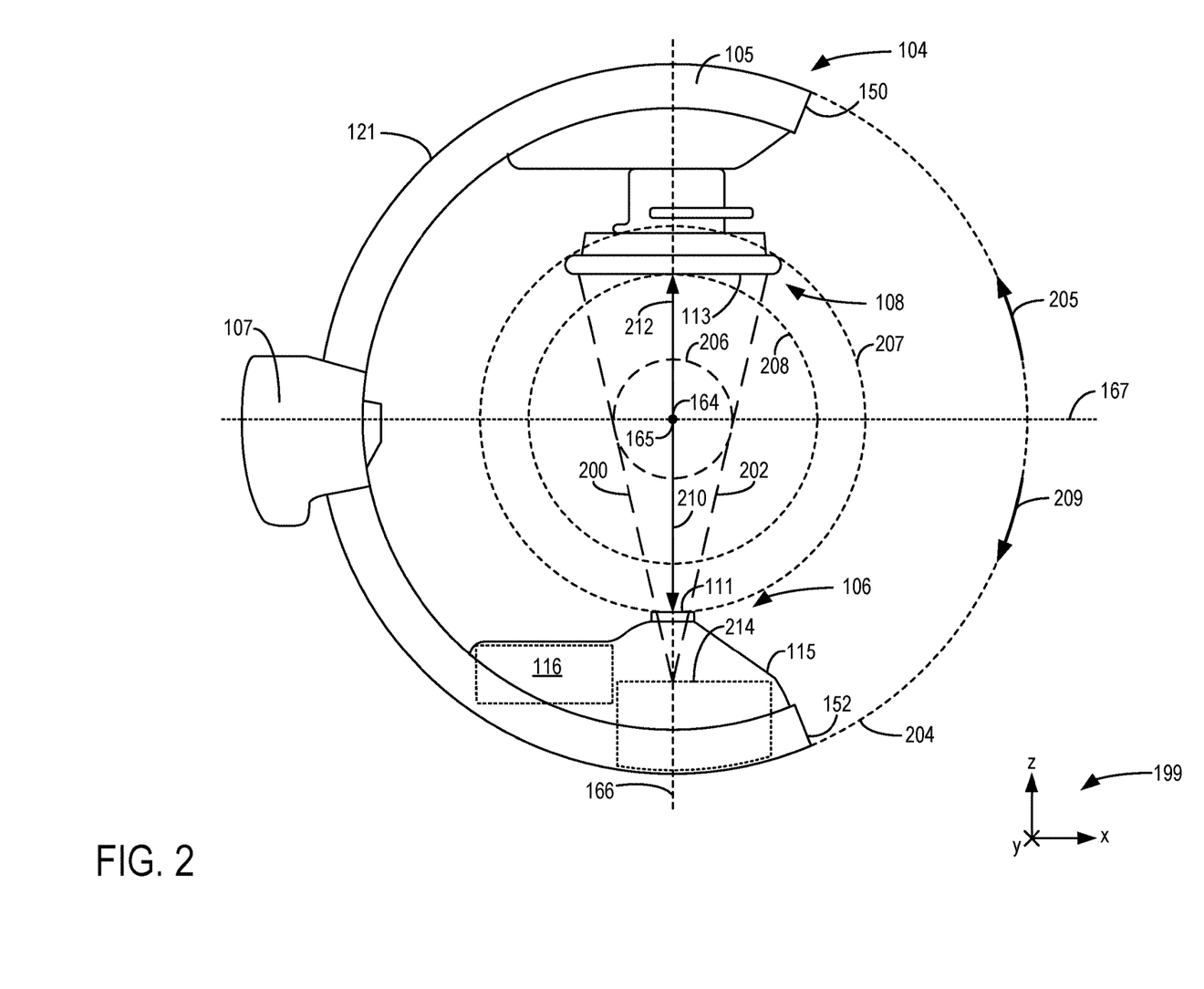
FIG. 2 is a partial view of the C-arm of FIG. 1 in a first position.
Figure 3:
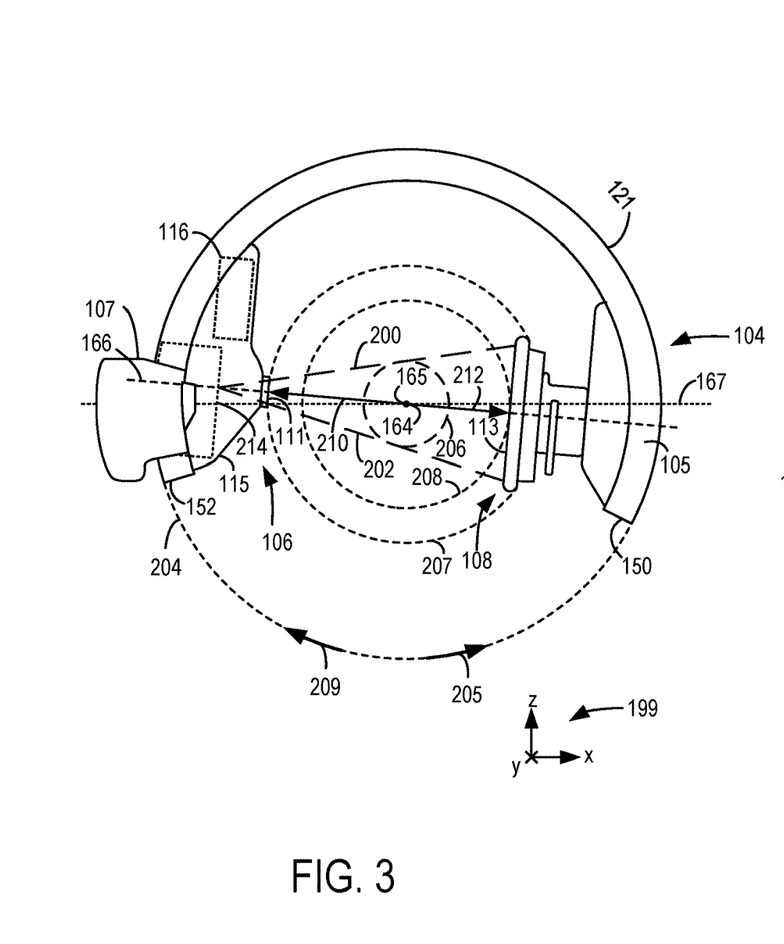
FIG. 3 is a partial view of the C-arm of FIGS. 1-2 in a second position.
Figure 4:
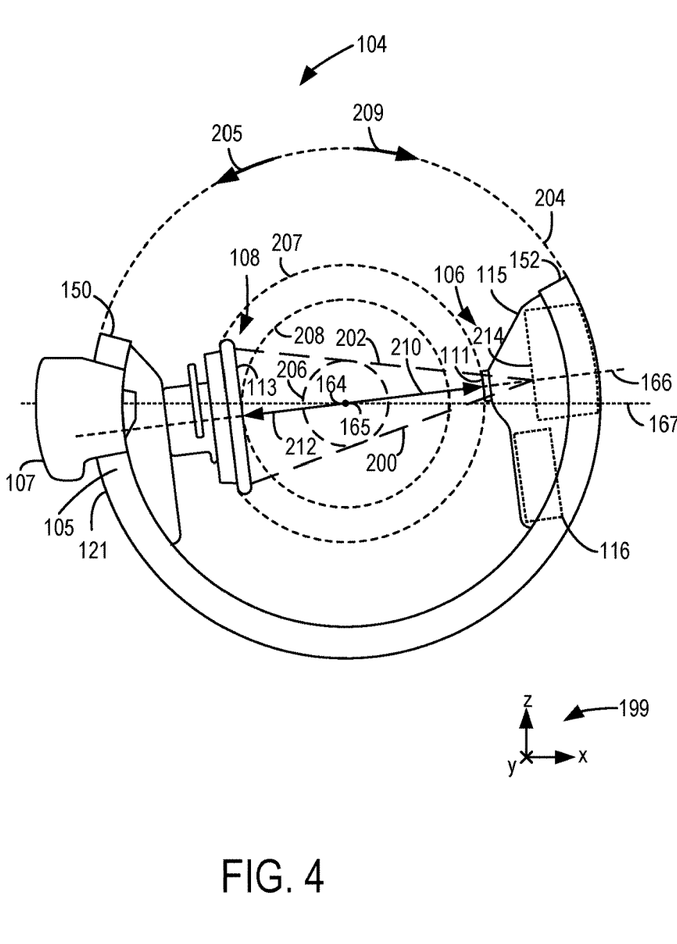
FIG. 4 is a partial view of the C-arm of FIGS. 1-3 in a third position.
Figure 5:
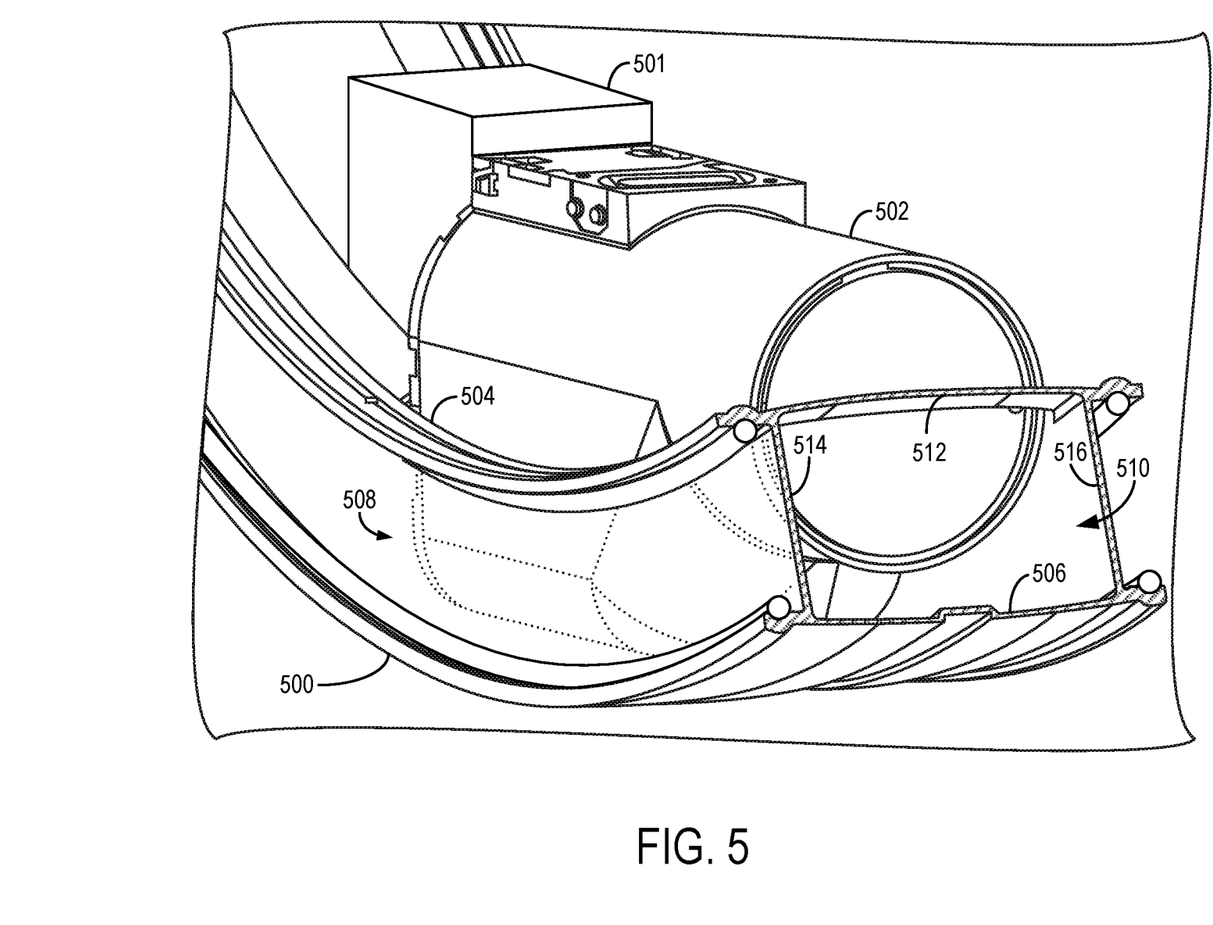
FIG. 5 is a perspective view of a portion of a C-arm housing and X-ray source.
Figure 6:
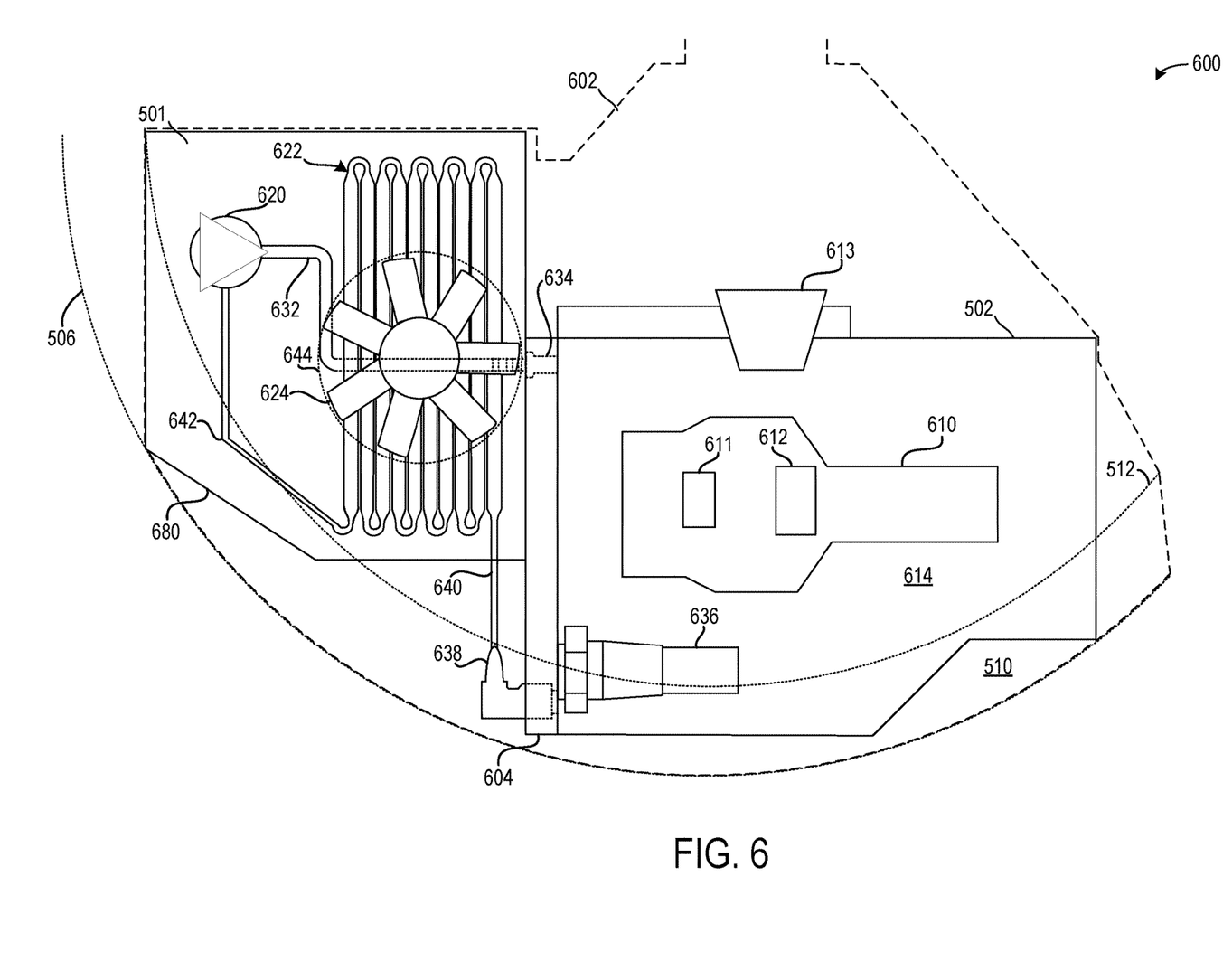
FIG. 6 shows a cross-sectional view of a cooling system and the X-ray source arranged within a casing and a portion of a main body of the C-arm housing.

FIG. 1 illustrates a side view of a medical imaging system comprising the X-ray source and the cooling arrangement arranged at a first end of an arm. A detector may be arranged at a second end of the arm, wherein the second end is opposite the first end. FIGS. 2 through 4 illustrate a movement of the arm. As shown, the cooling arrangement and the X-ray source remain adjacent one another through the movement of the arm. FIG. 5 illustrates a perspective view of the X-ray source and the cooling arrangement. FIG. 5 further illustrates a submersion of a portion of the X-ray source into the main body of the arm such that portions of the X-ray source are housed by walls of the arm, which limits passive cooling from surrounding environmental air. FIG. 6 illustrates a cross-section of the first end of the arm, which exposes interiors of the arm, the X-ray source, and the cooling arrangement.

FIGS. 1 to 6 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Referring to FIG. 1, a side view of a mobile medical imaging system 100 is shown, where the mobile medical imaging system includes a C-arm 104 with an x-ray source 106 positioned opposite to an x-ray detector 108. The imaging system 100 additionally includes a base unit 102. A base portion 156 of the base unit 102 includes a plurality of wheels 160 for supporting the mobile medical imaging system 100 and/or transporting the mobile medical imaging system 100 from one location to another. Each wheel 160 may include a brake configured to lock the wheel into a fixed position and reduce a likelihood of the movement of the mobile medical imaging system 100. Further, the base portion 156 includes a toe portion 157 extending in an outward direction relative to the base portion 156 and toward the C-arm 104 (e.g., parallel to a ground surface 190 on which the imaging system 100 sits). The toe portion 157 includes a vibration damping assembly 158, to which one or more of the wheels 160 is coupled. The vibration damping assembly 158 may comprise one or more damping elements. The vibration damping assembly 158 is configured to reduce vibrations in mobile medical imaging system 100 and to decrease a vibration decay time for vibrations which may arise from repositioning of C-arm 104 (e.g., rotation of the C-arm 104) and/or movement of imaging system 100 (e.g., from one location to another). It will be appreciated that in some examples of the mobile medical imaging system 100, the damping assembly 158 and other components related thereto may be omitted without departing from the scope of the present disclosure.

The C-arm 104 includes a C-shaped portion 105 connected to an extended portion 107. As an example, the C-shaped portion 105 may be configured to rotate at least 180 degrees in opposing directions (e.g., around a rotational axis 165). The C-shaped portion 105 is additionally rotatable about a rotational axis 164 via the extended portion 107. For example, the C-shaped portion 105 may be rotatably coupled to the extended portion 107 such that the C-shaped portion 105 may rotate relative to the extended portion 107 in a first direction 171 and/or an opposing, second direction 173 around the rotational axis 164. The C-shaped portion 105 may be rotated as described above in order to adjust the x-ray source 106 and detector 108 (positioned on opposite ends of the C-shaped portion of the C-arm 104 along an axis 166, where axis 166 intersects rotational axis 164 and extends radially relative to rotational axis 164) through a plurality of positions.

During an imaging operation, a portion of a patient's body placed in a clearance (e.g., gap) formed between the x-ray source 106 and detector 108 may be irradiated with radiation from the x-ray source. For example, x-ray source 106 may comprise an x-ray tube housed within a housing 115, and x-ray radiation generated by the x-ray source 106 may emit from an outlet 111 of the housing 115 and may be intercepted by a detection surface 113 of the detector 108. The radiation may penetrate the portion of the patient's body being irradiated and travel to the detector 108 where the radiation is detected. By penetrating the portion of the patient's body placed between the x-ray source 106 and detector 108, an image of the patient's body is captured and relayed to an electronic controller of the mobile medical imaging system 100 (e.g., via an electrical connection line, such as an electrically conductive cable 161). In one example, the display monitor may display images taken and processed by the mobile medical imaging system 100 as they are taken and during the imaging procedure (e.g., in real-time). Instructions may be entered into the imaging system 100 via one or more input devices. Instructions may include x-ray source activation instructions, source voltage/current instructions, source rotation instructions, image display instructions, image storing instructions, etc.

The base unit 102 may include the electronic controller (e.g., a control and computing unit) that processes instructions or commands sent from the user input devices during operation of the mobile medical imaging system 100. The base unit 102 may also include an internal power source (not shown) that provides electrical power to operate the imaging system 100. Alternatively, the base unit 102 may be connected to an external electrical power source to power the imaging system 100. A plurality of connection lines (e.g., electrical cables, such as electrically conductive cable 161) may be provided to transmit electrical power, instructions, and/or data between the x-ray source 106, detector 108, and the control and computing unit. The plurality of connection lines may transmit electrical power from the electrical power source (e.g., the internal and/or external source) to the x-ray source 106 and detector 108.

The C-arm 104 may be adjusted to a plurality of different positions by rotation of the C-shaped portion 105 of the C-arm 104 (e.g., via the coupling between the extended portion 107 and C-shaped portion 105). For example, in an initial, first position shown by FIG. 1, the detector 108 may be positioned vertically above the x-ray source 106 relative to the ground surface 190 on which the imaging system 100 sits, with axis 166 arranged normal to the ground surface 190 intersecting a midpoint of each of the outlet 111 of x-ray source 106 and detection surface 113 of detector 108. The C-arm 104 may be adjusted from the first position to a different, second position by rotating the C-shaped portion 105. In one example, the second position may be a position in which the x-ray source 106 and detector 108 are rotated 180 degrees together relative to the first position, such that the x-ray source 106 is positioned vertically above the detector 108, with axis 166 intersecting the midpoint of the outlet 111 of the x-ray source 106 and the midpoint of the detection surface 113 of the detector 108. When adjusted to the second position, the x-ray source 106 may be positioned vertically above the rotational axis 164 of the C-shaped portion 105 of the C-arm 104, and the detector 108 may be positioned vertically below the rotational axis 164.

As described above, the imaging system 100 includes X-ray source 106 positioned across rotational axis 164 relative to the detector 108. In the example shown by FIG. 1, detector 108 is positioned at a first end 150 of the C-shaped portion, and X-ray source 106 is positioned at an opposing, second end 152 of the X-ray source 106. In some examples, similar to those described further below, the C-shaped portion 105 includes an opening shaped to receive a casing (e.g., a housing) of the X-ray source 106. The X-ray source 106 may comprise an X-ray tube (e.g., a vacuum tube configured to produce X-ray radiation) housed within the casing, and the X-ray tube may be seated within a clearance formed between opposing walls of the C-shaped portion 105 through the opening.

That is to say, the X-ray tube may comprise a cathode and an anode arranged therein. The cathode may receive current, exciting electrons thereon which may then flow to the anode. This process may produce radiation used to pass through the outlet 111 to the detector 108. The X-ray source 106, including the X-ray tube, may be at least partially housed within the second end 152 of the main body 105. As such, at least a portion of the main body 105 may be hollow with space arranged therein to receive a portion of the X-ray source 106.

A cooling arrangement 116 may also be housed within the housing 115 and the second end 152 of the main body 105. Dashed line illustrates an imaginary division between the cooling arrangement 116 and the X-ray tube within the housing 115. An entirety of the cooling arrangement 116 is arranged at the second end 152 such that no portion of the cooling arrangement 116 extends beyond a profile of the housing 115. In one example, the housing 115 is a single continuous piece. Additionally or alternatively, outside of the outlet 111, the housing 115 may be completely sealed such that gases and liquids may not enter the housing 115. In one example, additionally or alternatively, the housing 115 is a continuation of the main body 105 such that the housing and second end 152 of the main body 105 are physically coupled to one another. The cooling arrangement and the X-ray tube within the housing 115 and the main body 105 are described in greater detail below.

By arranging the X-ray tube within the clearance of the C-shaped portion 105, a height of the X-ray source 106 (e.g., a length of the X-ray source 106 along axis 166 from the outlet 111 of the X-ray source 106 to the detector surface 113 of detector 108) may be reduced. The reduced height of the X-ray source 106 may increase an amount of open space between the detector surface 113 and the outlet 111 of the X-ray source 106, which may enable the C-arm 104 to accommodate larger patients for imaging and/or increase an ease of use of the C-arm 104 (e.g., increase an operating clearance of the C-arm 104) while maintaining the rotational axis 164 at the centered position between the first end 150 and the second end 152 (e.g., maintaining the rotational axis 164 an equal distance from each of the first end 150 and the second end 152 in the direction of axis 166). Additionally, by increasing the X-ray source 106 to detector surface 113 distance, a scan width may be improved along with a reduction in radiation dose penetrating a patient's skin. Maintaining the rotational axis 164 at the centered position may reduce a load (e.g., torque) on the C-shaped portion 105 during conditions in which the C-shaped portion 105 is rotated around the rotational axis 164 by reducing an eccentric motion of the C-shaped portion 105 relative to C-arms that do not include the rotational axis 164 at the centered position. As a result, a durability of the C-arm 104 may be increased and a likelihood of degradation of the C-arm 104 may be reduced.

Thus, in one example, FIG. 1 illustrates an embodiment of a mobile medical imaging system 100 comprising a first moveable portion and a second moveable portion. The first moveable portion may comprise the base unit 102 with a plurality of wheels 160 for moving the mobile medical imaging system 100 across a surface (e.g., the ground). The second moveable portion may comprise the C-arm 104, which is configured to rotate about an axis. In one example, the base unit 102 and the C-arm 104 are moveable independent of one another such that the base unit 102 may transport the mobile medical imaging system 100 without rotating the C-arm 104. Likewise, the C-arm 104 may rotate without moving the mobile medical imaging system 100 to a different location.

The cooling arrangement 116 is a fluid-circulating cooling arrangement in one example. The cooling arrangement 116 integrally arranged with the X-ray source 106 within the housing 111. This provides a compact design such that a size of the mobile medical imaging system 100 is not cumbersome to a user to transport through crowded hallways, doorways, small rooms, and the like. The cooling arrangement 116 is configured to flow fluid to an insert of the X-ray source which provides enhanced cooling relative to passive cooling features associated with previous examples of cooling systems of mobile medical imaging applications. In this way, the fluid-circulating cooling arrangement may at least solve a variety of technical issues prevalent to mobile medical imaging systems via improved temperature control with a relatively small packaging size and weight.

Referring collectively to FIGS. 2-4, various example positions of the C-shaped portion 105 are shown. Specifically, FIG. 2 shows the C-shaped portion 105 in a first position in which the axis 166 between the detector surface 113 and the outlet 111 of the X-ray source 106 is arranged perpendicular to the ground surface 190 on which the imaging system 100 sits (shown by FIG. 1, with axis 167 being an axis parallel to the ground surface 190 and perpendicular to a direction of gravity and rotational axis 164). FIG. 3 shows the C-shaped portion 105 in a first rotated position in which the X-ray source 106 is positioned closer to extended portion 107 and detector 108 is positioned further from extended portion 107 relative to the first position shown by FIG. 2, and FIG. 4 shows the C-shaped portion 105 in a second rotation position in which the detector 108 is positioned closer to the extended portion 107 and the X-ray source 106 is positioned further from the extended portion 107 relative to the first position. As one example, FIG. 3 may correspond to a rotation of the C-arm 104 by an angle of 45 degrees around the rotational axis 164 relative to the position shown by FIG. 2, and FIG. 4 may correspond to a rotation of the C-arm 104 by an angle of −45 degrees around the rotational axis 164 relative to the position shown by FIG. 2. In each of FIGS. 2-4, the extended portion 107 is maintained in position (e.g., not rotated) relative to the C-shaped portion 105, with the position of extended portion 107 in FIGS. 2-4 being the same as the position of extended portion 107 shown in FIG. 1 (e.g., with the extended portion 107 not rotated relative to the ground surface 190 or axis 167).

Each of FIGS. 2-4 show axis 200 and axis 202 illustrating a radiation emission pathway of the X-ray source 106. Specifically, the X-ray source 106 may emit a beam of X-ray radiation between the axis 200 and axis 202, where axis 200 and axis 202 represent outermost boundary of rays of the beam directed toward detector surface 113. As the C-shaped portion 105 rotates around the rotational axis 164 (e.g., for imaging of a patient or object to be imaged that is positioned at the rotational axis 164), the beam of X-ray radiation remains directed toward the detector surface 113 due to the concurrent rotation of each of the detector 108 and X-ray source 106 around the rotational axis 164. While rotating around the rotational axis 164, the C-shaped portion 105 may move along rotation pathway 204, and because the X-ray source 106 and detector 108 rotate around the rotational axis 164 along with the C-shaped portion 105, the beam of X-ray radiation emitted by the X-ray source 106 forms an isocentric imaging area 206 of the imaging system 100 (shown by FIG. 1, the imaging system 100 including C-arm 104). In other examples, the rotational axis 164 may not be isocentrically located relative to the C-shaped portion 105 of the C-arm 104.

For the examples depicted in FIGS. 1-4, the isocenter of the C-arm 104 is positioned at the rotational axis 164. Specifically, the isocenter of the C-arm 104 is positioned at an intersection of rotational axis 164 and axis 167. Each of the first end 150 and second end 152 may be positioned a same length from the isocenter. For example, an outer surface 121 of the C-shaped portion 105 may have a uniform radius of curvature in a direction around the rotational axis 164 (e.g., a same radius of curvature at each location along the outer surface 121 in the direction around the rotational axis 164, with the isocenter being the center of curvature) such that each portion of the outer surface 121, including portions positioned at the first end 150 and second end 152, is positioned a same distance from the isocenter along axis 166 (e.g., as indicated by rotation pathway 204 having a same radius of curvature as the outer surface 121). As described above, the C-shaped portion 105 may rotate around the rotational axis 164 via the coupling between the C-shaped portion 105 and the extended portion 107, and the C-shaped portion 105 may also rotate via the rotatable joint 109. During conditions in which the C-shaped portion 105 rotates via the rotatable joint 109, the C-shaped portion 105 may rotate around axis 167. In this configuration, the C-shaped portion 105 may rotate around either of rotational axis 164 or axis 167 (or both of rotational axis 164 and axis 167), where axis 167 is orthogonal to the rotational axis 164. In the views shown by FIGS. 2-4, however, the C-shaped portion 105 is rotated only around the rotational axis 164 and not the axis 167.

Although the first end 150 and second end 152 may be positioned the same length from the isocenter, each of detector surface 113 and outlet 111 may be positioned different lengths from the isocenter. For example, FIGS. 2-4 show a rotation pathway 207 of the outlet 111 and a rotation pathway 208 of the detector surface 113, with each of the rotation pathway 207 and rotation pathway 208 being of circular shape. Outlet 111 may move along rotation pathway 207 and detector surface 113 may move along rotation pathway 208 during conditions in which the C-shaped portion 105 is rotated around rotational axis 164. However, a length 212 (e.g., a diameter of the rotation pathway 208) from the isocenter to the detector surface 113 may be smaller than a length 210 (e.g., a diameter of the rotation pathway 207) from the isocenter to the outlet 111. As one example, the length 210 may be larger than the length 212 due to the X-ray source 106 being seated within a portion of the C-shaped portion 105. For example, X-ray tube 214 is shown schematically and illustrated by dashed lines in FIGS. 2-4 to indicate that the X-ray tube 214 is housed within housing 115 and seated within a portion of the C-shaped portion 105.

The seated position of the X-ray tube 214 within the C-shaped portion 105 may enable the outlet 111 to be positioned closer to the second end 152 compared to configurations in which the X-ray tube is not seated within the C-shaped portion, which may result in a decreased height of the X-ray source 106 (e.g., a decreased height of housing 115 of the X-ray tube 214). As described above, the resulting reduced height of the X-ray source 106 may increase the amount of open space between the detector surface 113 and outlet 111 (e.g., increase the length 210 between the isocenter and the outlet 111 relative to the length 212 between the isocenter and the detector surface 113), which may enable the C-arm 104 to accommodate larger patients and/or increase ease of use of the C-arm 104.

Further, in some examples, the seated position of the X-ray source 106 within the C-shaped portion 105 may increase the balance of the C-arm 104 during isocentric rotation (e.g., symmetric rotation around the isocenter, as described above). As one example, the seated position of the X-ray source 106 may provide counterweight to a weight of the detector 108, such that a load and/or vibration of a motor of the imaging system driving the rotation of the C-arm 104 is reduced compared to configurations that do not include the X-ray source 106 seated within the C-shaped portion 105.

Referring now to FIG. 5, a perspective view of a second end of a C-shaped portion 500 of a C-arm of an imaging system is shown. In one example, the second end of the C-shaped portion 500 may be the second end 152 of the C-shaped portion 105 described above with reference to FIGS. 1-4. The C-shaped portion 500 includes an opening 504 shaped to receive an X-ray tube 502 and a cooling arrangement 501, where the X-ray tube 502 is seated within the C-shaped portion 500 against an interior surface of an outer circumferential wall 506 (e.g., as illustrated by broken lines 508 indicating a position of the X-ray tube 502 within an interior clearance 510 of the C-shaped portion 500). In some examples, the X-ray tube 502 may be the X-ray tube 214 described above with reference to FIGS. 2-4. Additionally or alternatively, the cooling arrangement 501 may be the cooling arrangement 116 of FIGS. 1-4.

As illustrated, the cooling arrangement 501 may be spaced away from the outer circumferential wall 506 such that a bottom of the cooling arrangement 501 does not touch the outer circumferential wall 506. However, the cooling arrangement 501 may be arranged such that it is at least partially arranged within the interior clearance 510. The portions of the X-ray tube 502 and the cooling arrangement 501 arranged outside of the interior clearance 510 may be covered via a housing, such as housing 115 of FIG. 1.

The interior clearance 510 of the C-shaped portion 500 is a hollow portion of the C-shaped portion 500 formed by each of the outer circumferential wall 506, inner circumferential wall 512, first sidewall 514, and second sidewall 516. The opening 504 is formed through the inner circumferential wall 512 from an exterior surface 518 of the inner circumferential wall 512 to the interior clearance 510. In some examples, the interior clearance 510 may extend an entire length of the C-shaped portion 500 from a first end to a second end (e.g., similar to first end 150 and second end 152 described above), and the interior clearance 510 may be closed at both ends of the C-shaped portion 500. Additionally or alternatively, the interior clearance may extend only as far as a circumferential length of the opening 504. In one example, the opening 504 is sized and shaped to receive only the housing of the cooling arrangement 501 and the X-ray tube 502. In some examples, an entirety of the X-ray tube 502 may be positioned within the interior clearance 510. In other examples, a different amount of the X-ray tube 502 (e.g., at least half of the X-ray tube 502) may be positioned within the interior clearance 510.

Turning now to FIG. 6, it shows a cross-section 600 of the X-ray tube 502 and the cooling arrangement 501. The cross-section 600 further includes housing 602, which may be a non-limiting example of housing 115 of FIG. 1. The housing 602 may be a single, continuous piece configured to separate shield each of the X-ray tube 502 and the cooling arrangement 501.

As illustrated, the housing 602, illustrated in larger dashes, may house an entirety of the X-ray tube 502 and the cooling arrangement 501. As such, no components of the cooling arrangement 501 and the X-ray tube 502 may extend beyond a profile of the housing 602. The housing 602 may be further shaped to contain bottom portions of the X-ray tube and the cooling arrangement 501 such that the housing 602 is at least partially positioned within the clearance 510 and in face-sharing contact with the outer circumferential wall 506, illustrated via smaller dashes. Larger dashes are larger than smaller dashes. As such, if service of the X-ray tube 502 and/or cooling arrangement 501 is desired, the entire housing 602 may be removed from the first end of the C-arm, resulting in the removal of both the cooling arrangement 501 and the X-ray tube 502.

The cooling arrangement 501 may be coupled to the X-ray tube 502 via an interface 604. As shown, the interface 604 may be physically coupled to each of the cooling arrangement 501 and the X-ray tube 502. The interface 604 comprises a plurality of ports fluidly coupling the cooling arrangement 501 to an interior volume 614 of the X-ray tube 502. In one example, an X-ray insert 610 comprising a cathode 611 and an anode 612 may be arranged in the X-ray tube 502. The cathode 611 may be configured to receive current from a connector, which may excite electrons on the cathode 611 and cause them to flow toward the anode 612. This may result in radiation which may exit the X-ray insert 610 toward an outlet 613, and to a detector 108. In one example, the interface 604 may be further shaped to receive one or more conductors of the connector to flow current to the cathode 611. Additionally or alternatively, the interface 604 may be one example of a high-voltage connector, comprising conductive pins for physically coupling the interface 604 to the X-ray tube 502. Additionally or alternatively, the conductors may be maintained separate from cooling fluids passing through the interface 604 from the cooling arrangement 501 to the X-ray tube 502.

The cooling arrangement 501 comprises a pump 620, a passage of radiator coils 622, and a fan 624. The pump 620 may be one or more of a hydraulic, pneumatic, electric, and mechanical pump. In one example, the pump 620 is electric. The pump 620 may pressurize and direct a cooling fluid through a pump outlet passage 632 to the interior volume 614 of the X-ray tube 502. In one example, the cooling fluid is dielectric oil, however, other cooling fluids may be used without departing from the scope of the present disclosure. As illustrated, the pump outlet passage 632 may be arranged between the fan 624 and the radiator coils 622. A first adapter 634 may extend through the interface 604, wherein the first adapter 634 may fluidly couple the pump outlet passage 632 to the interior volume 614 of the X-ray tube 602. The first adapter 634 may be shaped to sealingly engage with the pump outlet passage 632 so that all liquid in the pump outlet passage 632 flows into the interior volume 614.

As shown, the interior volume 614 receives liquid from an upper region, above the X-ray insert 610. As such, the liquid may flow down and at least partially fill the interior volume 614. A second adapter 636 is illustrated at a lower region of the interior volume 614. In one example, the second adapter 636 comprises two connector bodies, wherein a first connector body is configured to allow external cabling to connect to the cathode 611 and the anode 612 of the X-ray insert 610. A second connector body may be configured to expel liquid from the interior volume 614 to a spigot 638 fluidly coupled to an intermediate passage 640.

The intermediate passage 640 is fluidly coupled to a first tube of the radiator coils 622. Liquid in the radiator coils 622 may reverse in flow direction as it moves from the first tube to a second tube. In one example, the liquid in the radiator coils reverses flow direction at it passes to a neighboring tube. In one example, the radiator coils 622 may serpentine. The liquid may exit the radiator coils 622 at a lower region near the inner circumferential wall 512 before flowing upward though a pump inlet passage 642. The pump inlet passage 642 is fluidly coupled to the pump 620.

In one example, the individual tubes of the radiator coils 622 may be parallel with one another, wherein U-shaped tubes may fluidly couple neighboring tubes. The U-shaped tubes may invert a coolant flow as coolant flows from one tube to another.

Optionally, a suction device may be arranged in a lower region of the interior volume 614 adjacent to the second adapter 636. In one example, the suction device is adjacent to the inner circumferential wall 512. In some examples, the suction device 636 may be arranged adjacent to the outer circumferential wall 506. The example of FIG. 6 merely illustrates one example of the X-ray tube 502 being positioned within the clearance 510. It will be appreciated that a greater portion or a smaller portion of the X-ray tube 502 may be arranged within the clearance 510 than that depicted in FIG. 6.

The suction device may utilize vacuum, which may be generated via the pump 620 or via an auxiliary device, to draw liquid out of the interior volume 614 and to a spigot 638 fluidly coupled to an intermediate passage 640. Additionally or alternatively, the suction device may be an ancillary device which may produce suction independently of the pump 620.

The fan 624 may be configured to rotate such that a breeze is generated. In one example, the breeze may cool liquid in the radiator coils 622 and in the pump outlet passage 632. By arranging the pump outlet passage 632 between the radiator coils 622 and the fan 624, a cooling effect experience by liquid in the pump outlet passage 632 may be increased relative to liquid in the radiator coils 622, which may enhance cooling. In one example, a vent 644 is arranged within the housing 602 such that air within the cooling arrangement 501 may be released to atmosphere. In one example, the cooling arrangement 501 may be arranged in a casing 680 configured to block gas transfer between the cooling arrangement 501 and the X-ray tube 502. That is to say, fluids outside of the pump outlet passage 632 and the suction device 636 may not flow between the cooling arrangement 501 and the X-ray tube 502. The vent 644 arranged on a portion of the casing 680 behind the radiator coils 622. The fan 624 may draw air from another vent (not illustrated) on an opposite wall of the casing 680 relative to the vent 644, wherein the fan 64 propels the air across the pump outlet passage 632 and the radiator coils 622.

More specifically, the vent 644 may comprise a circular shape with its center concentrically located with a center of the fan 624. A diameter of the vent 644 may be slightly larger than a diameter of the fan 624. By doing this, external environmental air, relative to an interior of the casing 680 and the housing 602, may be drawn via the fan 624 and blown across the radiator coils 622 and the pump outlet passage 632 through a further vent arranged opposite to the vent 644. In one example, the further vent is shaped and sized identically to the vent 644 and is arranged directly opposite to the vent 644 through the casing 680 and the housing 602.

In one example, the cooling arrangement 501 is configured to fill an entire volume of the interior volume 614 with a cooling fluid. In this way, bubbles and other artifacts that may disrupt an image acquisition quality may be limited.

The cooling arrangement 501 may be activated, which may include activating the pump 620 in response to a cooling demand from the X-ray tube 502. Alternatively, the cooling arrangement 501 may remain in operation at all times when the X-ray tube 502 is also in operation. In one example, the X-ray tube 502 may comprise a temperature sensor configured to sense a temperature of a portion of the X-ray tube 502. In one example, the temperature sensor may sense a temperature of the fluid within the interior volume 614 or of the exterior surface of the X-ray tube 502. Additionally or alternatively, the pump 620 may be activated in response to a threshold time elapsed following a start of a scanning procedure. In one example, the threshold time elapsed is a fixed value. Alternatively, the threshold time elapsed is a dynamic value, which may be adjusted based on scan type, current flow, previous scan duration, and time elapsed between a previous scan and a current scan. For example, the threshold time elapsed may decrease as the time elapsed between the previous scan and the current scan decreases.

In this way, an entirety of the cooling arrangement 501 and the X-ray tube 502 are arranged within the housing 602 and adjacent to the first end of the C-arm of the X-ray system. As such, other portions of the C-arm, including the second end, are free of any components of the cooling arrangement 501. In one example, the cooling arrangement 501 is limited to being located to only within a boundary of the housing 602 and does not extend beyond the boundary of the housing 602. Additionally or alternatively, passages of the cooling arrangement 501 are routed through only the cooling arrangement 501, the interface 604, and into the X-ray tube 502.

Thus, in one aspect, a mobile X-ray device may comprise a C-arm comprising an X-ray source arranged at a first end and a detector arranged at a second end, opposite the first end. A cooling arrangement 501 may be arranged only at the first end within a housing of the X-ray source. The technical effect of arranging an entirety of the cooling arrangement 501 adjacent to the X-ray source is to integrate the fluid circulating coolant arrangement on a mobile X-ray system without limiting a range of motion of the C-arm. Due to space constraints typically associated with the mobile X-ray system, wherein the space constraints are due to hallway width, room size, doorway size, and the like, previous examples of the mobile X-ray systems may include only passive cooling arrangements with cold plates, fans, heat spreaders, and the like. Previously, circulating fluid cooling arrangements were only arranged on fixed room X-ray systems, which may mechanistically feasible due to little restriction with regard to size constraints as the fixed room X-ray systems were not configured to move.

The integrated cooling arrangement of the present disclosure enables a mobile X-ray system to receive circulated cooling fluids. This may enhance cooling relative to the passive cooling arrangements commonly arranged on previous examples of mobile X-ray systems. Furthermore, a mobility of the mobile X-ray system is not limited due to a relatively small packaging size and weight of the integrated cooling arrangement. Additionally, a mobility of the C-arm to which the integrated cooling arrangement is coupled may not be limited.

An embodiment of a mobile X-ray system, comprises a base unit comprising one or more wheels configured to support and transport the mobile X-ray system, a moveable arm comprising an X-ray source arranged at a first end and an X-ray detector arranged at a second end, and a fluid-circulating cooling arrangement arranged within a housing shared with the X-ray source, wherein passages of the cooling arrangement do not extend outside the housing.

A first example of the mobile X-ray system further includes where the cooling arrangement is directly adjacent to and integrated with the X-ray source.

A second example of the mobile X-ray system, optionally including the first example, further includes where the moveable arm comprises a clearance, and wherein the X-ray source and the cooling arrangement are at least partially positioned within the clearance.

A third example of the mobile X-ray system, optionally including one or more of the previous examples, further includes where the moveable arm is coupled to the base unit.

A fourth example of the mobile X-ray system, optionally including one or more of the previous examples, further includes where the cooling arrangement comprises a pump, a fan, a serpentine passage, a pump outlet passage, and a pump inlet passage, and wherein each of the pump, the fan, the radiator coils, the pump outlet passage, and the pump inlet passage are arranged within the housing at the first end.

A fifth example of the mobile X-ray system, optionally including one or more of the previous examples, further includes where the pump outlet passage is configured to flow liquid from the pump to an interior volume of the X-ray source.

A sixth example of the mobile X-ray system, optionally including one or more of the previous examples, further includes where the moveable arm moves independently of the base unit.

A seventh example of the mobile X-ray system, optionally including one or more of the previous examples, further includes where the pump outlet passage is arranged between the fan and the radiator coils.

An embodiment of an X-ray device, comprises a cooling arrangement comprising a pump fluidly coupled to a pump outlet passage and a pump inlet passage, a fan, and a plurality of radiator coils, wherein the pump outlet passage is arranged between the plurality of radiator coils and the fan, an X-ray source arranged within a housing configured to house an entirety the X-ray source and the cooling arrangement at an end of a moveable C-arm.

A first example of the X-ray device further includes where the moveable C-arm comprises an interior space between its walls in which the X-ray source and the cooling arrangement are arranged, wherein the housing comprises an outlet, and wherein the housing completely seals the X-ray source from atmosphere except for the outlet.

A second example of the X-ray device, optionally including the first example, further includes where the cooling arrangement is arranged only at the end of the moveable C-arm adjacent to the end.

A third example of the X-ray device, optionally including one or more of the previous examples, further includes where the end is a first end, further comprising a second end opposite the first end, wherein an X-ray detector is arranged at the second end, wherein a portion of the C-arm between the housing and the second end is free of cooling arrangement components.

A fourth example of the X-ray device, optionally including one or more of the previous examples, further includes where the X-ray device is a mobile X-ray device comprising a base unit with wheels, wherein the base unit is free of cooling arrangement components.

A fifth example of the X-ray device, optionally including one or more of the previous examples, further includes where an interface is arranged directly between the cooling arrangement and the X-ray source.

An embodiment of a mobile imaging system, comprises a base unit capable of being moved within a room and from room to room, a C-arm coupled to the base unit including an X-ray source at a first end and a detector at a second end opposite the first end, wherein the C-arm comprises an interior clearance separating an inner circumferential wall and an outer circumferential wall, and an opening arranged in the inner circumferential wall shaped to receive the X-ray source and a cooling arrangement, wherein the cooling arrangement is fluidly coupled to an interior volume of the X-ray source via a pump outlet passage.

A first example of the mobile imaging system further includes where a housing is configured to house each of the X-ray source and the cooling arrangement.

A second example of the mobile imaging system, optionally including the first example, further includes where the housing extends through the opening and is pressed against interior surfaces of the outer circumferential wall.

A third example of the mobile imaging system, optionally including one or more of the previous examples, further includes where the housing is arranged only at the first end, and wherein all components of the cooling arrangement and the X-ray source are contained within the housing.

A fourth example of the mobile imaging system, optionally including one or more of the previous examples, further includes where components of the cooling arrangement comprise a pump, a plurality of radiator coils, a fan, a pump outlet passage, a pump inlet passage, and an intermediate passage.

A fifth example of the mobile imaging system, optionally including one or more of the previous examples, further includes where the C-arm is configured to rotate around a rotational axis arranged between the first end and the second end, further comprising a base unit configured to support the mobile imaging system and transport the mobile imaging system to different locations, wherein the C-arm and the base unit move independent of one another.

As used herein, an element or step recited in the singular and proceeded with the word "a" or "an" should be understood as not excluding plural of said elements or steps, unless such exclusion is explicitly stated. Furthermore, references to "one embodiment" of the invention do not exclude the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A mobile X-ray system, comprising:
   a base unit comprising one or more wheels configured to support and transport the mobile X-ray system;
   a moveable arm comprising an X-ray source arranged at a first end and an X-ray detector arranged at a second end, wherein the moveable arm comprises a clearance, wherein the clearance does not extend to the first end of the moveable arm, and
   a fluid-circulating cooling arrangement having a pump arranged within a housing shared with the X-ray source at the first end of the moveable arm;
   wherein the fluid-circulating cooling arrangement includes passages for circulating a fluid therethrough;
   wherein the pump circulates the fluid through the passages and into an interior volume of the X-ray source.

2. The mobile X-ray system of claim 1, wherein the fluid-circulating cooling arrangement is directly adjacent to and integrated with the X-ray source.

3. The mobile X-ray system of claim 1, wherein the X-ray source and the cooling arrangement are at least partially positioned within the clearance.

4. The mobile X-ray system of claim 1, wherein the moveable arm is coupled to the base unit.

5. The mobile X-ray system of claim 4, wherein the moveable arm moves independently of the base unit.

6. The mobile X-ray system of claim 1, wherein the fluid-circulating cooling arrangement further comprises, a fan, a plurality of radiator coils, a pump outlet passage, and a pump inlet passage, and wherein each of the fan, the plurality of radiator coils, the pump outlet passage, and the pump inlet passage are arranged within the housing.

7. The mobile X-ray system of claim 6, wherein the pump outlet passage is configured to flow the fluid from the pump to the interior volume of the X-ray source.

8. The mobile X-ray system of claim 6, wherein the pump outlet passage is arranged between the fan and the plurality of radiator coils.

9. The mobile X-ray system of claim 1, wherein the fluid is dielectric oil.

10. The Mobile X-ray system of claim 1, wherein an interface is arranged directly between the fluid-circulating cooling arrangement and the X-ray source.

11. An X-ray device, comprising:
    a cooling arrangement comprising a pump fluidly coupled to a pump outlet passage and a pump inlet passage, a fan, and a plurality of radiator coils, wherein the pump outlet passage is arranged between the plurality of radiator coils and the fan; and
    an X-ray source arranged within a housing configured to house an entirety of the X-ray source and the cooling arrangement only at one end of a moveable C-arm, wherein an interface is arranged directly between the cooling arrangement and the X-ray source through which the pump circulates a liquid coolant into an interior volume of an X-ray tube of the X-ray source.

12. The X-ray device of claim 11, wherein the moveable C-arm comprises an interior space between at least three walls in which the X-ray source and the cooling arrangement are arranged, wherein the housing comprises an X-ray outlet, and wherein the housing encloses the X-ray source, except for air transfer through the cooling arrangement.

13. The X-ray device of claim 11, further comprising a second end opposite the first end, wherein an X-ray detector is arranged at the second end, wherein a portion of the C-arm between the housing and the second end is free of cooling arrangement components.

14. The X-ray device of claim 11, wherein the X-ray device is a mobile X-ray device comprising a base unit with wheels, wherein the base unit is free of cooling arrangement components.

15. The mobile X-ray system of claim 11, wherein the liquid coolant is dielectric oil.

16. A mobile imaging system, comprising:
    a base unit for moving within a room and from room to room;
    a C-arm coupled to the base unit including an X-ray source at a first end and a detector at a second end opposite the first end, wherein the C-arm comprises an interior clearance separating an inner circumferential wall and an outer circumferential wall; and
    an opening arranged in the inner circumferential wall, shaped to receive the X-ray source and a cooling arrangement, wherein the opening does not extend to the first end of the C-arm arm, wherein the cooling arrangement is fluidly coupled to an interior volume of the X-ray source via a pump outlet passage, wherein a housing is configured to house each of the X-ray source and the cooling arrangement; and
    wherein the housing is arranged only at the first end, and wherein all components of the cooling arrangement and the X-ray source are contained within the housing.

17. The mobile imaging system of claim 16, wherein the housing extends through the opening and is pressed against interior surfaces of the outer circumferential wall.

18. The mobile imaging system of claim 16, wherein components of the cooling arrangement comprise a pump, a plurality of radiator coils, a fan, a pump outlet passage, a pump inlet passage, and an intermediate passage.

19. The mobile imaging system of claim 16, wherein the C-arm is configured to rotate isocentrically around a rotational axis arranged between the first end and the second end, and the base unit is configured to support the mobile imaging system and transport the mobile imaging system to different locations, wherein the C-arm and the base unit move independent of one another.

20. The Mobile imaging system of claim 16, wherein an interface is arranged directly between the cooling arrangement and the X-ray source through which the pump circulates a liquid coolant into an interior volume of an X-ray tube of the X-ray source.

* * * * *